United States Patent
Stango et al.

(12) 
(10) Patent No.: US 9,717,566 B2
(45) Date of Patent: Aug. 1, 2017

(54) ADJUSTABLE DENTAL PROPHYLAXIS ANGLE WITH AXIALY SHIFTABLE ADJUSTMENT MECHANISM

(71) Applicant: HU-FRIEDY MFG. CO., LLC, Chicago, IL (US)

(72) Inventors: James Christopher Stango, Chicago, IL (US); Charles Jerome Saslow, Highland Park, IL (US); Rachel Calian Trautvetter, Evanston, IL (US); Karen Leigh Neiner, Chicago, IL (US); Steven Rodney Walding, Chicago, IL (US); Albert Anthony Schenk, III, Trevor, WI (US)

(73) Assignee: HU-FRIEDY MFG. CO., LLC, Chicago, IL (US)

( * ) Notice: Subject to any disclaimer, the term of this patent is extended or adjusted under 35 U.S.C. 154(b) by 93 days.

(21) Appl. No.: 14/606,515

(22) Filed: Jan. 27, 2015

(65) Prior Publication Data

US 2016/0213445 A1    Jul. 28, 2016

(51) Int. Cl.
*A61C 1/12* (2006.01)
*A61C 17/00* (2006.01)

(52) U.S. Cl.
CPC .............. *A61C 1/12* (2013.01); *A61C 17/005* (2013.01)

(58) Field of Classification Search
CPC ................................ A61C 1/12; A61C 17/005
See application file for complete search history.

(56) References Cited

U.S. PATENT DOCUMENTS

| | | | |
|---|---|---|---|
| 219,849 | A | 9/1879 | Cushing |
| 636,476 | A | 11/1899 | Webster |
| 1,170,524 | A | 2/1916 | Fernald |
| 1,379,880 | A | 5/1921 | Seaborn |
| 4,278,429 | A | 7/1981 | Straihammer et al. |
| 4,303,393 | A | 12/1981 | Gentry |

(Continued)

FOREIGN PATENT DOCUMENTS

| | | |
|---|---|---|
| DE | 519472 C | 2/1931 |
| FR | 1068328 A | 6/1954 |

(Continued)

OTHER PUBLICATIONS

Search Report for International application No. PCT/US2016/014881, mailed Apr. 4, 2016.

(Continued)

*Primary Examiner* — Rex R Holmes
(74) *Attorney, Agent, or Firm* — Marshall, Gerstein & Borun LLP

(57) ABSTRACT

A dental prophylaxis angle having a tool head and a hand piece includes an adjustment mechanism, which allows the tool head to be angularly adjusted between a plurality of angular positions relative to the hand piece. The tool head is axially shiftable relative to the hand piece between a locked position and an adjustment position. In the locked position, the tool head is prevented from shifting angularly relative to the hand piece. In the adjustment position, the tool head may be selectively pivoted relative to the hand piece and thereby angularly adjusted. A spring may be provided to urge the tool head into the locked position at one or more of the angular positions.

16 Claims, 7 Drawing Sheets

(56) References Cited

U.S. PATENT DOCUMENTS

| | | |
|---|---|---|
| 5,150,495 A | 9/1992 | Discko, Jr. et al. |
| 5,433,605 A | 7/1995 | Strobl, Jr. |
| 5,699,810 A | 12/1997 | Pallikaris et al. |
| 5,902,107 A | 5/1999 | Lowell |
| 6,050,989 A | 4/2000 | Fox et al. |
| 6,053,732 A | 4/2000 | Sale |
| 7,422,433 B2 | 9/2008 | Carron et al. |
| 8,123,523 B2 | 2/2012 | Carron et al. |
| 8,360,774 B2 | 1/2013 | Carron et al. |
| 8,459,992 B2 | 6/2013 | Carron et al. |
| 8,597,022 B2 | 12/2013 | Carron et al. |
| 8,668,494 B2 | 3/2014 | Carron et al. |
| 8,814,566 B2 | 8/2014 | Carron et al. |
| 8,834,159 B2 | 9/2014 | Carron et al. |
| 2007/0233567 A1 | 10/2007 | Daly |
| 2008/0220392 A1 | 9/2008 | Carron et al. |
| 2010/0015568 A1* | 1/2010 | Carron ............... A61C 1/12 433/130 |
| 2010/0196847 A1 | 8/2010 | Carron et al. |
| 2012/0214126 A1 | 8/2012 | Carron et al. |
| 2012/0315598 A1 | 12/2012 | Kim |
| 2015/0335395 A1 | 11/2015 | Boehm |

FOREIGN PATENT DOCUMENTS

| | | |
|---|---|---|
| KR | 101317310 B1 | 10/2013 |
| WO | WO-2008109750 A2 | 9/2008 |
| WO | WO-2009043059 A1 | 4/2009 |

OTHER PUBLICATIONS

Written Opinion for International application No. PCT/US2016/014881, mailed Apr. 4, 2016.
Search Report for International application No. PCT/US16/13522 mailed Mar. 21, 2016.
Written Opinion for International application No. PCT/US16/13522 mailed Mar. 21, 2016.

* cited by examiner

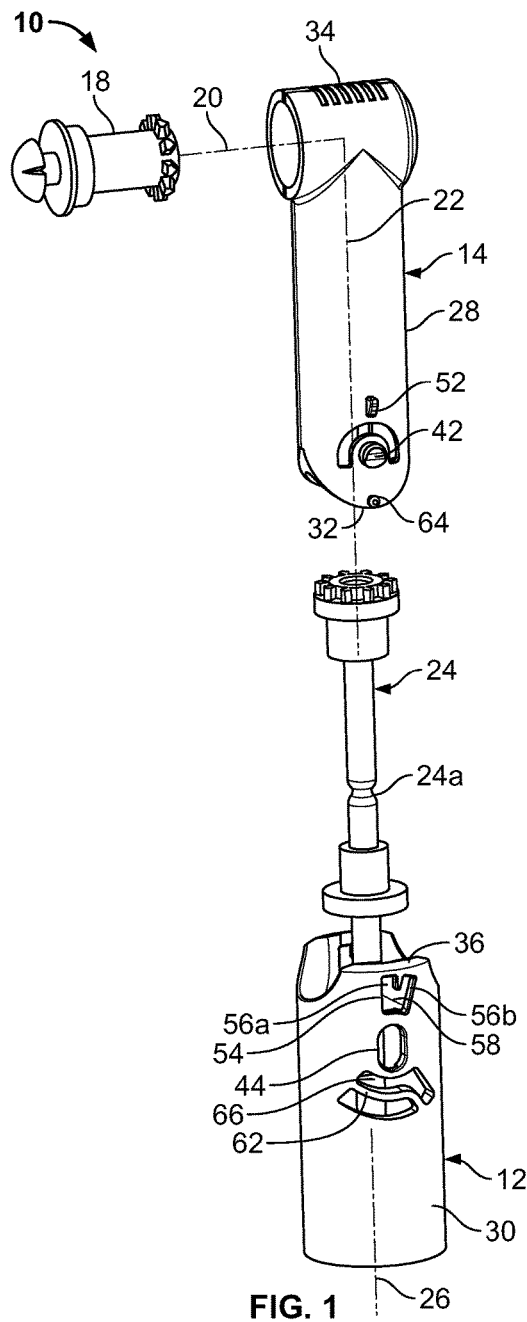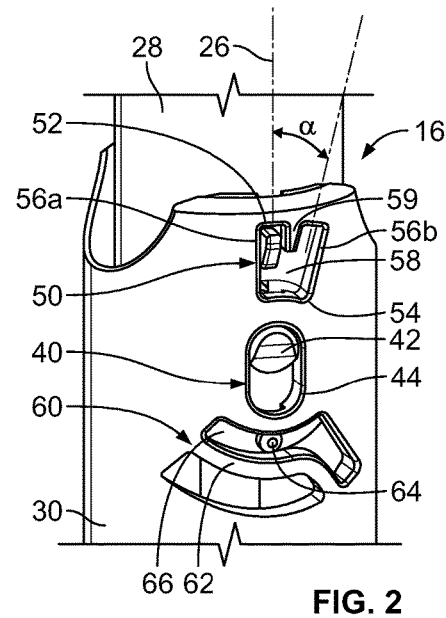
FIG. 1
FIG. 2

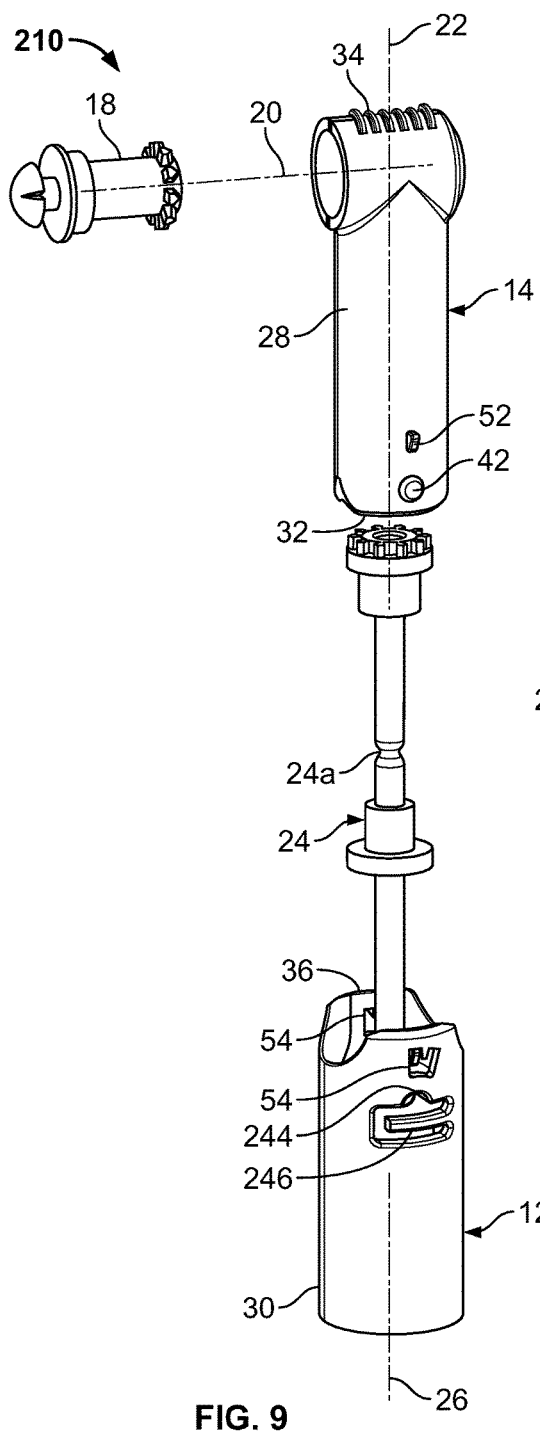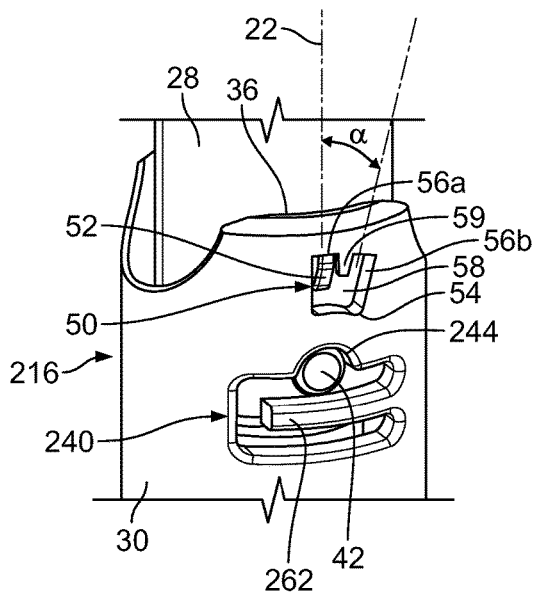
FIG. 10
FIG. 9

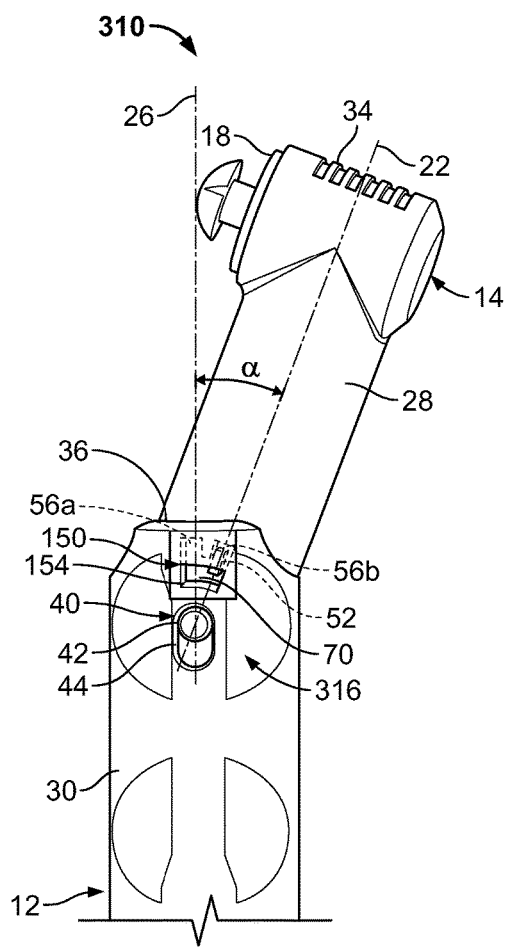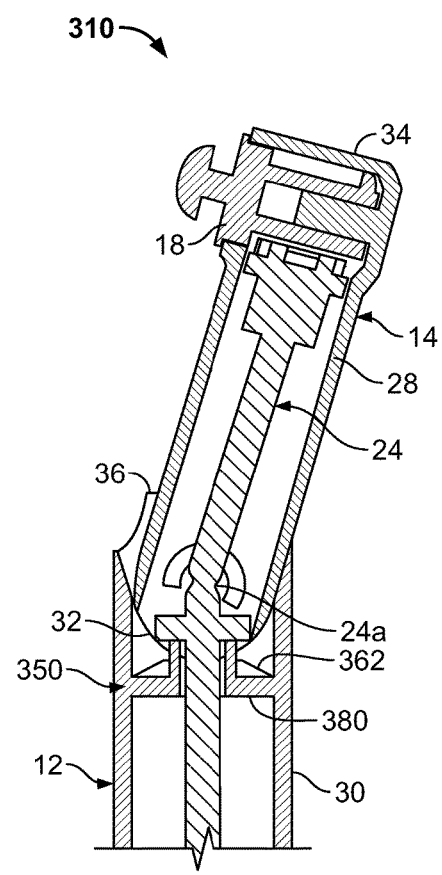
FIG. 13
FIG. 14

… (1)

ADJUSTABLE DENTAL PROPHYLAXIS ANGLE WITH AXIALY SHIFTABLE ADJUSTMENT MECHANISM

FIELD OF THE DISCLOSURE

The present invention relates to a dental prophylaxis angle having an adjustment mechanism to adjust an angle of the tool head relative to the hand piece.

BACKGROUND

A dental prophylaxis angle (also frequently called simply a "prophy angle") is a dental/medical instrument generally having a hand piece to be gripped by a user, such as a dentist or surgeon, and a tool head that carries a tool drive upon which a tool, such as a dental or surgical tool, is or may be mounted. The tool drive is arranged in such manner that the tool extends at an angle, often a right angle, to a longitudinal axis of the hand piece and/or the tool head. Sometimes the hand piece and the tool head are provided in a straight configuration, i.e., coaxially aligned along a single longitudinal axis. Sometimes, the tool head is provided in an angled configuration, i.e., wherein the longitudinal axis of the tool head is angled laterally in relation to the longitudinal axis of the hand piece.

Adjustable prophy angles are known that include a mechanism that allows the tool head to be selectively adjusted angularly, for example, between a straight configuration and an angled configuration. However, the adjustment mechanisms for known adjustable prophy angles are often relatively complex and/or cause or require unwanted movements between the tool head and the hand piece.

SUMMARY

According to some aspects, a dental prophylaxis angle having a tool head and a hand piece includes an adjustment mechanism, which allows the tool head to be angularly adjusted between a plurality of angular positions relative to the hand piece. The tool head is axially shiftable relative to the hand piece between a locked position and an adjustment position. In the locked position, the tool head is prevented from shifting angularly relative to the hand piece. In the adjustment position, the tool head may be selectively pivoted relative to the hand piece and thereby angularly adjusted.

According to some aspects, the angle of the tool head relative to the hand piece may be selectively adjusted by a user by urging the tool head axially toward or away from the hand piece into the adjustment position, pivoting the tool head from a first angular position to a second angular position while in the adjustment position, and optionally allowing the spring to urge the tool head axially into a locked position in the second position.

The adjustable dental prophylaxis angle may optionally include any one or more of the additional arrangements and/or features either singly or in combination.

In some arrangements, the adjustment mechanism includes a pivot assembly that pivotably and slidably connects the tool head to the hand piece. The pivot assembly may allow the tool head and the grip to be axially pushed together or pulled apart and to pivot relative to each other. The pivot assembly may include a pivot member that is pivotably received within a pivot receptacle. The pivot member may be slidably received within the pivot receptacle. The pivot member may be in the form of a pin carried by the tool head or the hand piece. The pivot receptacle may be in the form of an elongate recess in the other of the tool head or the hand piece. The elongate recess may be in the form of a slot, which extends completely through a wall, and/or in the form of a groove, which extends only partially into the wall. The pivot receptacle may be formed in an exterior wall or another wall. In one arrangement, the pivot member is carried by the tool head, and the pivot receptacle is carried by the hand piece. The pivot receptacle may have a longitudinal axis that is aligned with an axis of the hand piece, and the pivot member is able to slide along the longitudinal axis. The pivot receptacle may be in the form of a partial or open-sided socket, having a wall portion defining a groove to pivotably receive the pivot member and an open portion opposite the recess. A spring may be disposed opposite the groove to resiliently urge the pivot member into the groove. Other arrangements of a pivot assembly that allows the tool head to both shift axially relative to the hand piece and to pivot angularly relative to the hand piece may also be used.

In some arrangements, the adjustment mechanism may include a spring assembly that is arranged to urge the tool head into the locked position at one or more of the angular positions. The tool head may be urged axially relative to the grip against the force of the spring to unlock the mechanism, for example, by pushing the two pieces toward each other or by pulling the two pieces away from each other. When unlocked, the tool head may be pivoted about the pivot assembly to pivotably adjust the tool head between a plurality of angular positions relative to the hand piece. Preferably, after the angle of the tool head is adjusted to a selected second angular position, the spring may automatically urge the tool head and the hand piece axially back into the locked position at the selected angular position.

The spring may be carried by the tool head and/or the hand piece. The spring may take any effective form to urge the hand piece and the tool head into a locked position. The spring may urge the grip and the tool head axially away from each other, or the spring may urge the grip and the tool head axially toward each other, depending on the arrangement of the remaining portions of the adjustment mechanism that define which direction causes the tool head and the grip to lock into a selected angular position and to be adjusted between angular positions.

In some arrangements, the spring includes a resilient member formed by a portion of a wall of the hand piece. The resilient member may be formed along a transverse track in a wall of the hand piece. The resilient member may be in the form of a resilient wall section extending along a cutout in a wall, such as an outer wall, of a housing of the hand piece arranged to be gripped by a user. The resilient member may directly engage the pivot member to urge the tool head toward the locked position. The resilient member may engage a spring follower spaced apart from the pivot member. The spring follower may be a pin carried by the tool head. The spring follower may engage the resilient member to urge the tool head and the grip into the locked position at one or more, and preferably each of the plurality of angular positions. The resilient wall section may be arcuate so as to extend along an arcuate path of the pin as the tool head and the grip are pivoted about the pivot assembly.

In some arrangements, the spring may be carried on a spring seat. The spring seat may be disposed within the hand piece. The spring may be arranged to press against the tool head, such as against the proximal end of the tool head. The spring may be in the form of a bowed disc, such as a washer that is bowed out of plane, that resiliently flexes into or toward planarity. The spring seat may be in the form of an inner annular shoulder in the grip.

The adjustment mechanism may include an angular lock assembly arranged to releasably lock the tool head in any selected one of the predefined angular positions relative to the hand piece when the tool head is in the locked position. The angular lock assembly may be arranged to allow the tool head to be axially shifted relative to the hand piece between a locked position and an adjustment position. The angular lock assembly may be arranged to allow the tool head to be angularly adjusted between the plurality of angular positions relative to the hand piece in the adjustment position. In some arrangements, the angular lock assembly includes a tab and a receiver arranged to lockingly receive the tab at each of the plurality of predefined angular positions. The receiver may include a plurality of locking slots defined in one of the hand piece and the tool piece. Each locking slot may correspond to a different one of the predefined angular positions. Each locking slot is adapted to lockingly receive the tab therein in the locked position so as to prevent pivoting of the tool head relative to the hand piece. The receiver may be associated with the hand piece. The receiver may be defined by and/or carried by the hand piece, such as in a wall of the housing of the hand piece. The receiver may include a first locking slot arranged to lock the tool head in a straight position, in which a longitudinal axis of the tool head is axially aligned with a longitudinal axis of the hand piece. The receiver may include a second locking slot arranged to lock the tool head in an angled position, in which the longitudinal axis of the tool head is angularly offset laterally from the longitudinal axis of the hand piece. The receiver may include a third or additional locking slots at other angled positions. The locking slots may be connected to each other by one or more transverse tracks, which are aligned generally transverse to the axes of one or both of the tool head and the hand piece, and along which the tab may travel as the tool head is pivoted at the pivot assembly. The locking slots may be disposed at spaced apart locations along the transverse track. The lock receivers may extend radially outwardly from the transverse track. The first locking slot may be aligned along the axis of the hand piece. The second locking slot may be aligned at an angular offset from the longitudinal and axis of the hand piece, thereby having a V-shaped arrangement. The first and second locking slots may be angularly offset from each other by an almost infinite number of angles only as may be limited by other mechanisms, such as a drive mechanism joint, of the prophy angle. The first and second locking slots preferably are angularly offset between about 1 degree and 90 degrees, more preferably between about 5 degrees and about 45 degrees, and even more preferably between 10 degrees and 25 degrees, and most preferably about 17 degrees; however any angular offset within the mechanically acceptable range of the other mechanisms may be used.

In some arrangements, the prophy angle includes a drive linkage. The drive linkage may operatively connect a motor with a tool drive. The motor may be carried in the hand piece. The motor may be driven by electrical power, compressed air, hydraulic power, or any other power arrangement arranged for operatively driving the motor of the prophy angle. The tool drive may be carried by the tool head. The tool drive may be carried at a distal end of the tool head. The tool drive may have a rotational axis that is aligned transverse to, such as perpendicular to, a longitudinal axis of the tool head. The drive linkage may include a flexible joint, such that the drive linkage is capable of driving the tool drive in any of the selected angular positions. The tool drive may be arranged to carry a tool, such as a polishing head or other rotational tool, for operating on a patient.

Additional aspects and arrangements are apparent upon review of the following description and the accompanying drawings.

BRIEF DESCRIPTION OF THE DRAWINGS

FIG. 1 is an exploded partial side view of an adjustable dental prophylaxis angle according to one arrangement;

FIG. 2 is an enlarged partial side view of an adjustment mechanism of the prophy angle of FIG. 1;

FIG. 9 is an exploded partial side view of an adjustable dental prophylaxis angle according to a further arrangement;

FIG. 10 is an enlarged partial side view of an adjustment mechanism of the prophy angle of FIG. 9;

FIG. 13 is a partial side view of an adjustable dental prophylaxis angle according to yet another arrangement; and FIG. 14 is a partial longitudinal cross-sectional view of the adjustable dental prophylaxis angle of FIG. 13.

DETAILED DESCRIPTION OF THE DRAWINGS

Figure 3:
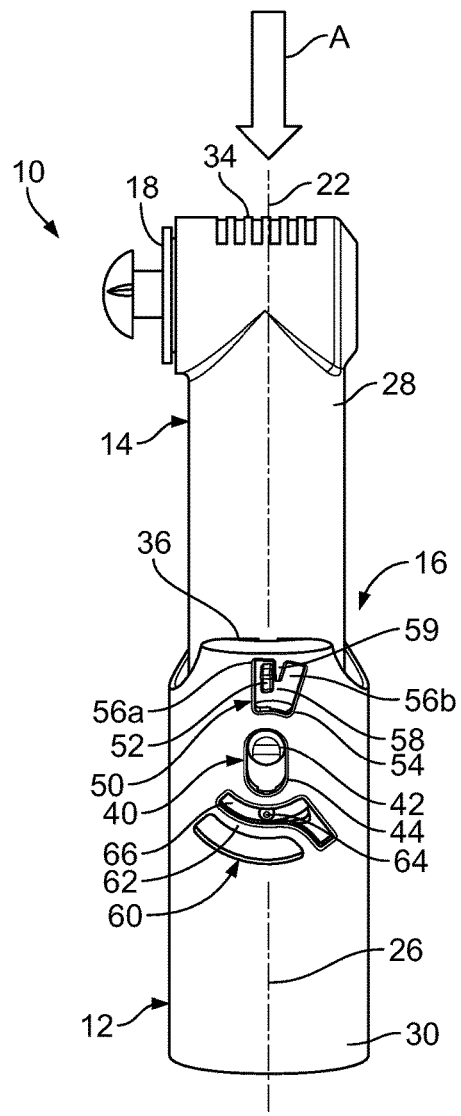
FIG. 3 is a partial side view of the prophy angle of FIG. 1 in a straight angular position.

Turning now to FIGS. 1-4, an adjustable dental prophylaxis angle 10 (hereinafter, "prophy angle") includes a hand piece 12, a tool head 14 pivotably coupled to the hand piece so as to pivot laterally about a pivot axis, and an adjustment mechanism 16 (best seen in FIG. 2), which allows the tool head 14 to be angularly adjusted about the pivot axis among a plurality of angular positions relative to the hand piece 12. In the present example, the tool head 14 can be pivotably adjusted between a first angular position and a second angular position. In this example, the first angular position is a straight position (as seen for example in FIGS. 1 and 3), and the second angular position is an angularly bent position (as seen for example in FIG. 4). In the straight position, a first axis 22 along the longitudinal axis of the tool head 14, is substantially aligned with, and may be coaxial with, a second axis 26 along the longitudinal axis of the hand piece 12. In the bent position, the first axis 22 is angularly offset laterally from the second axis 26 an angle $\alpha$. The angle $\alpha$ is preferably between 0 degrees and 90 degrees, and the present arrangement is approximately 17 degrees; however the angle $\alpha$ is not limited to any particular one of these values and may include additional values at least within the rate these ranges and/or outside these ranges.

The prophy angle 10 may take any of various forms and arrangements, for example, suitable and/or desired for performing oral procedures on a patient. For example, in the present exemplary arrangement, a tool drive 18 is operatively carried by the tool head 14. The tool drive 18 is preferably a rotating tool drive which rotates about an axis 20. The tool drive 18 is preferably disposed such that the axis 20 is transverse to, such as perpendicular to and through, a first longitudinal axis 22 of the tool head 14. A drive unit, such as a motor (not shown), may be carried by the hand piece 12. The drive unit may be powered by any power source, such as electrical, compressed air, or hydraulic, sufficient to operate the prophy angle 10 in a usual and customary manner. A drive linkage 24 operatively connects the drive unit with the tool drive 18 such that operation of the drive unit drives the tool drive 18 for operative use of the prophy angle 10. The drive linkage 24 preferably has a flexible joint 24a that allows the drive linkage 24 to operatively drive the tool drive 18 in both the straight position (as seen for example in FIGS. 1 and 3) and in the angularly bent position (as seen for example in FIG. 4). The flexible joint 24a is preferably aligned with the pivot axis between the hand piece 12 and the tool head 14. The tool head 14 preferably includes a housing 28, and the hand piece 12 preferably includes a housing 30. The housing 28 extends longitudinally along the first axis 22 between a proximal end 32 and the distal and 34. The tool drive 18 is disposed at the distal end 34, and a first portion of the adjustment mechanism 16 is disposed at the proximal and 32. The housing 30 extends longitudinally along the second axis 26 from a proximal end (not shown) to a distal end 36. The drive unit may be disposed at the proximal and, and a second portion of the adjustment mechanism 16 is disposed at the distal and 36. The drive linkage 24 extends longitudinally along interior bores of the housing 30 and the housing 28 to operatively connect the drive unit with the tool drive 18. In this arrangement, the housing 30 forms an exterior surface of the hand piece 12, and is preferably arranged to provide an easy gripping surface for the hand of a user. The housing 28 also forms an exterior surface of the tool head 14, and is preferably arranged suitably for being inserted into a patient's mouth to perform a desired procedure therein. However, except as otherwise expressed herein, the prophy angle is not necessarily limited to the specific exemplary arrangement shown in the drawings, but rather other arrangements of the prophy angle are also possible in accordance with the teachings of the present disclosure.

Focusing now on the adjustment mechanism 16, as best seen in FIG. 2, the adjustment mechanism 16 includes a pivot assembly 40 that pivotably and slidably connects the tool head 14 to the hand piece 12. The pivot assembly 40 includes a pivot member 42 and a pivot receptacle 44 at the pivot axis. The pivot member 42 is pivotably received within the pivot receptacle 44 such that the tool head 14 may be pivoted laterally with respect to the second axis 26 of the hand piece 12 about the pivot axis. The pivot member 42 is slidably received within the pivot receptacle 44 such that the tool head 14 and the hand piece 12 may be pushed together or pulled apart generally axially. In this arrangement, the pivot member 42 is carried by the housing 28 of the tool head 14, and the pivot receptacle 44 is defined in the housing 30 of the hand piece 12. The pivot member 42 is disposed near the proximal and 32 of the housing 28. The pivot member 42 is in the form of a pin projecting laterally outwardly from the housing 28. The pivot receptacle 44 is disposed near the distal and 36 of the housing 30. The pivot receptacle 44 is in the form of an elongate slot, which extends between a distal end and a proximal end. The pin and the elongate slot are preferably aligned along and/or define the pivot axis between the hand piece 12 and the tool head 14. The pivot member 42 can slide longitudinally along the elongate slot between the distal end in the proximal end of the pivot receptacle 44. The elongate slot is aligned axially with the second axis 26 of the housing 30 such that the pivot member 42 can slide axially with respect to the housing 30 of the hand piece 12. In other arrangements, the pivot receptacle 44 may be in the form of a groove on an interior surface of the housing 30, which does not extend completely through the housing 30. Other arrangements of the pivot assembly 40 that pivotably and slidably connected the tool head 14 to the hand piece 12 are also contemplated.

The adjustment mechanism 16 preferably includes an angular lock assembly 50. The angular lock assembly 50 allows the tool head 14 to be selectively locked in any one of a plurality of pre-defined angular positions relative to the hand piece 12. The angular lock assembly 50 allows the tool head 14 to be axially shifted relative to the hand piece 12 between a locked position and an adjustment position. The angular lock assembly 50 allows the tool head 14 to be angularly adjusted between a plurality of selected angular positions relative to the hand piece 12 in the adjustment position. The angular lock assembly 50 locks the tool head 14 in a selected one of the angular positions when the tool head is in the locked position. In the present example, the angular lock assembly 50 is arranged to allow the tool head 14 to be selectively locked in either of a first angular position or a second angular position. The first angular position is the straight position shown in FIG. 3, and the second angular position is the bent position shown in FIG. 4; however, different angular positions and/or additional angular positions are also possible. In the present arrangement, the lock assembly 50 includes a tab 52 or similar projection and a receiver 54 arranged to lockingly receive the tab 52 at each of the plurality of angular positions. The receiver 54 is includes a first locking slot 56a and a second locking slot 56b defined adjacent the distal end 36 of the housing 30, between the distal end of the pivot receptacle 44 and the distal end of the housing 30. The first locking slot 56a and the second locking slot 56b are arranged in a generally V-shaped form, with the first locking slot aligned axially with the first position, and the second locking slot 56b aligned axially with the second position. The first locking slot 56a and the second locking sloth 56b preferably are connected or merge at their proximal ends, for example by a transverse track 58. A dividing wall 59 separates the distal ends of the locking slots 56a, 56b from each other. The tab 52 is carried by the housing 28 of the tool head 14 and spaced apart distally from the pivot member 42. The tab 52 projects outwardly into the receiver 54. The tab 52 can slide axially along and within each of the locking slots 56a and 56b. In the locked position, the pivot member 42 is disposed at the distal end of the pivot receptacle 44, and the tab 52 is angularly locked within either one of the locking slot 56a or the locking slot 56b. In the adjustment position, the pivot member 42 is disposed at the proximal end of the pivot receptacle 44, and the tab 52 can be shifted laterally between the locking slots 56a and 56b along the transverse track 58. In this example, the locking slot 56a is aligned with the second axis 26, and the locking slot 56b is disposed at the angle α, which in this arrangement is approximately 17 degrees, laterally offset from the second axis 26. Of course, other angular alignments may be used. Additional angular positions may be provided, for example by providing additional locking slots at additional angular offsets. Other arrangements of the angular lock assembly 50 may be used which allow the tool head 14 to be axially shifted relative to the hand piece 12 between a locked position and an adjustment position and which allow the tool head 14 to be angularly adjusted between a plurality of selected angular positions relative to the hand piece 12 in the adjustment position and which lock the tool head 14 in a selected one of the angular positions when the tool head is in the locked position.

The adjustment mechanism 16 preferably includes a spring assembly 60. The spring assembly 60 is arranged to urge the tool head 14 into the locked position under normal conditions. The spring assembly 60 is also arranged to allow the tool head 14 to be urged into the adjustment position, for example by pushing the tool head 14 axially toward the hand piece 12 or by pulling the tool head 14 axially away from the hand piece 12. In the present arrangement, the spring assembly 60 is arranged to resiliently urge the tool head 14 axially away from the hand piece 12 and into the locked position. However, the spring assembly 60 is also arranged to allow a user to push the tool head 14 axially toward the hand piece 12 into the adjustment position, preferably by simply pressing the two parts together with his or her two hands, without requiring an unreasonable amount of force, for example during in oral or dental procedure. Further, the spring assembly 60 is preferably arranged to automatically urge the tool head 14 axially back into the locked position at a selected angular position when the user stops pushing the tool head 14 in the hand piece 12 axially together. In the present arrangement, the spring assembly 60 includes a spring 62 and a spring follower 64. The spring 62 is formed by a resilient portion of the wall of the housing 30. Portions of the wall of the housing 30 spaced proximally from the pivot receptacle 44 are cut away to define a lateral spring member, as best seen in FIG. 2, which may be resiliently flexed along the longitudinal axis of the housing 30. The spring follower 64 is formed by a protrusion, such as a knob or pin, projecting outwardly from the housing 28 of the tool head 14. The spring follower 64 is disposed between the pivot member 42 and the proximal end 32 of the housing 28. The spring follower 64 rests against the spring 62 such that the spring 62 can urge the tool head 14 into the locked position by engaging against the spring follower 64. The spring 62 extends laterally along a lateral track 66 in the form of a transverse slot or cutout from the wall of the housing 30. The spring follower 64 moves laterally along the spring 62 in the lateral track 66 when the tool head 14 is pivotably adjusted between the angular positions. The spring 62 has an arcuate shape so as to extend along an arcuate path of the spring follower 64 as the tool head 14 is pivotably adjusted. However, other arrangements for the spring 62 and/or the entire spring assembly 60 may be used in accordance with the teachings of the present disclosure.

Figure 4:
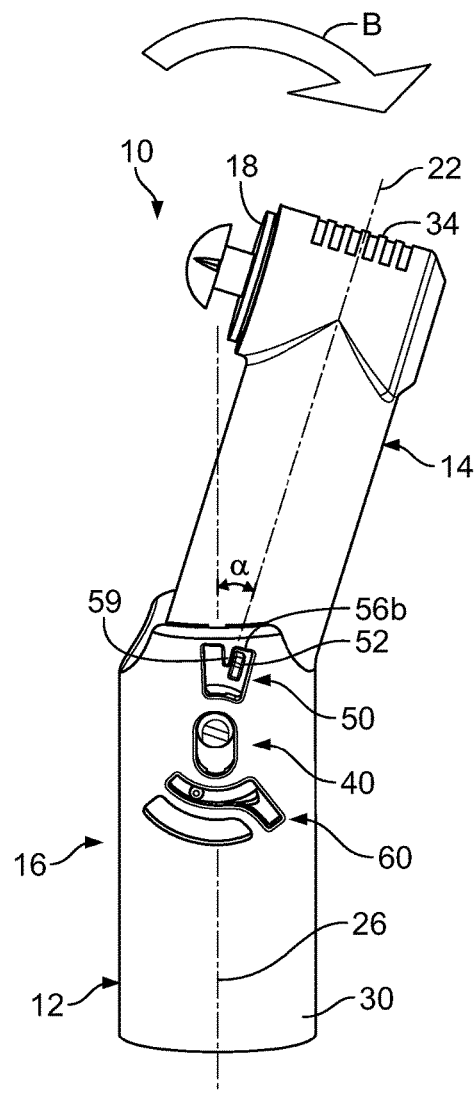
FIG. 4 is a partial side view of the prophy angle of FIG. 1 in a bent angular position.
Figure 5:
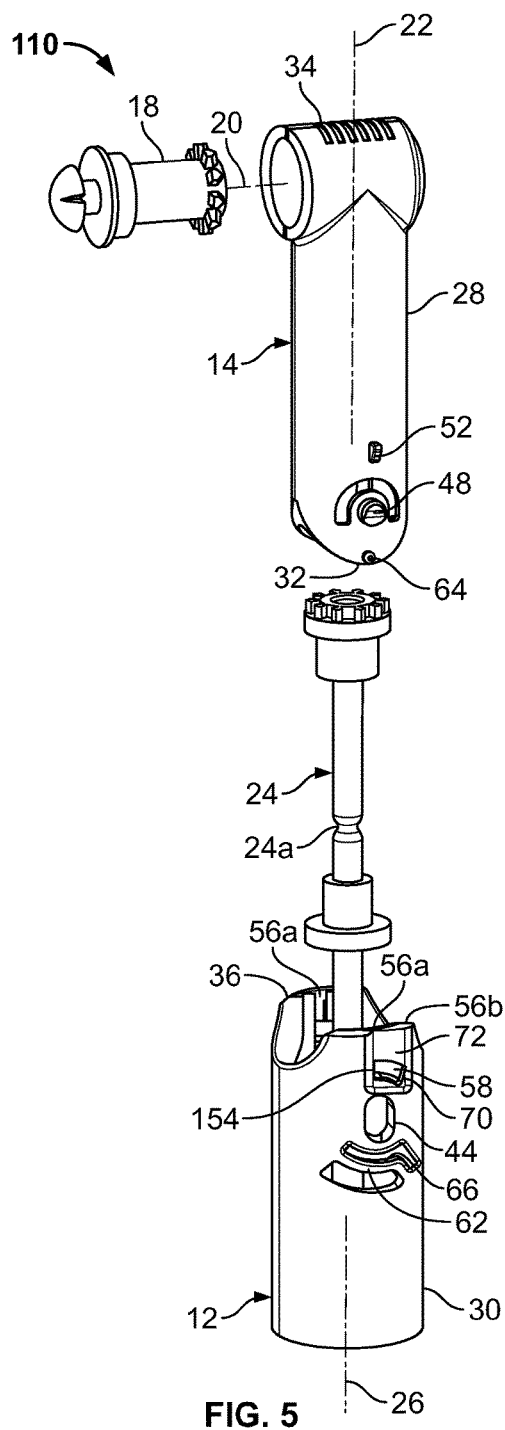
FIG. 5 is an exploded partial side view of an adjustable dental prophylaxis angle according to another arrangement.

Next, a process of adjusting the prophy angle 10 is described with reference to FIGS. 3 and 4. Beginning at FIG. 3, the prophy angle 10 is locked in a first angular position, which in this example is a straight position. The tool head 14 is in the locked position, with the spring 62 pushing the spring follower 64 upwardly, which urges the pivot member 42 upwardly against the distal end of the pivot receptacle 44 and which urges the tab 52 upwardly into the distal end of the locking slot 56a, thereby locking the tool head 14 in the first angular position. In order to adjust the tool head 14 to the second angular position shown in FIG. 4, first, the tool head 14 is pressed axially toward the hand piece 12 as shown by the arrow A of FIG. 3 into the adjustment position. This action simultaneously presses the spring follower 64 downwardly against the spring 62, slides the pivot member 42 downwardly in the pivot receptacle 44 to the proximal end of the pivot receptacle 44, and slides the tab 52 downwardly toward the transverse track 58 of the receiver 54. Once in the adjustment position, the tool head 14 is pivoted laterally angularly about the pivot assembly 40 the angle α as shown by the arrow B until the tool head is in the second angular position shown in FIG. 4. As the tool head 14 is pivoted, the tab 52 shifts laterally along the transverse track 58, the pivot member 42 pivots within the pivot receptacle 44, and the spring follower 64 slides along the spring 62 in the lateral track 66, all until the tab 52 is aligned with the locking slot 56b. After the tool head 14 has been pivoted into the second angular position, the axial pressure applied to the tool head 14 may be released, at which point the spring 62 urges the tool head 14 back into the locked position, but now in the second angular position as shown in FIG. 4. In so doing, the spring 62 urges the spring follower 64 upwardly toward the distal end 36 of the housing 30, which simultaneously slides the pivot member 42 axially along the pivot receptacle 44 toward the distal end of the pivot receptacle 44 and slides the tab 52 upwardly into the locking slot 56b. In the locked position, the dividing wall 59 between the distal ends of the locking slots 56a and 56b prevent the tool head 14 from undesirably pivoting laterally out of the selected first angular position or second angular position without sliding the tool head 14 axially into the adjustment position at described above.

In the drawings, the adjustment mechanism 16 is fully visible on only one side of the prophy angle 10. Preferably, the adjustment mechanism 16 includes an identical arrangement on the opposite side, which is not fully visible in the drawings. In this preferred arrangement, for example, first and second pivot members 42 are received within respective first and second receptacles 44, disposed on opposite sides of the housings 28 and 30. The pivot members 42 preferably defined a transverse pivot axis. The transverse pivot axis may extend perpendicularly through the second axis 26 and the first axis 22, or the transverse pivot axis may be offset from one or both of the first and second axes 22, 26. Other portions of the adjustment mechanism 16 may optionally also be mirrored on the opposite side of the hand piece 12 and the tool head 14. However, in some arrangements, one or more portions of the adjustment mechanism 16 may be included on only one of the sides of the prophy angle 10.

FIGS. 5-8 exemplify another prophy angle 110 according to the teachings of the present application. The prophy angle 110 is similar to the prophy angle 10 except for differences in the adjustment mechanism 116 as explained in detail hereinafter. Thus, the prophy angle 110 also includes a tool head 14 that is pivotably and slidably coupled to a hand piece 12, wherein the tool head 14 can be selectively adjusted between a plurality of pre-selected angular positions including a first angular position, such as a straight position (see FIG. 7), and a second angular position, such as a bent position (see FIG. 8). The prophy angle 110 also includes a flexible drive linkage 24 that operatively connects a drive unit carried in the hand piece 12 with a tool drive 18 carried by the tool head 14. These and other remaining features of the prophy angle 110 that are not otherwise described hereinafter are substantially similar to the same features as described previously with respect to the prophy angle 10, and the reader is invited to refer to such description for additional details related thereto.

Figure 6:
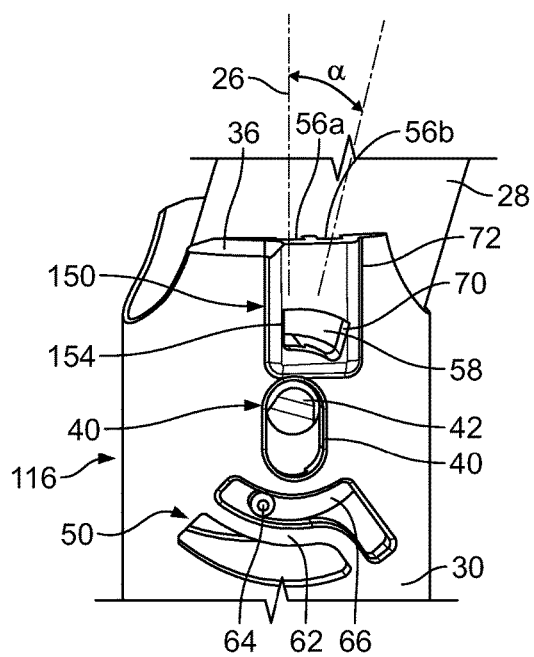
FIG. 6 is an enlarged partial side view of an adjustment mechanism of the prophy angle of FIG. 5.
Figure 7:
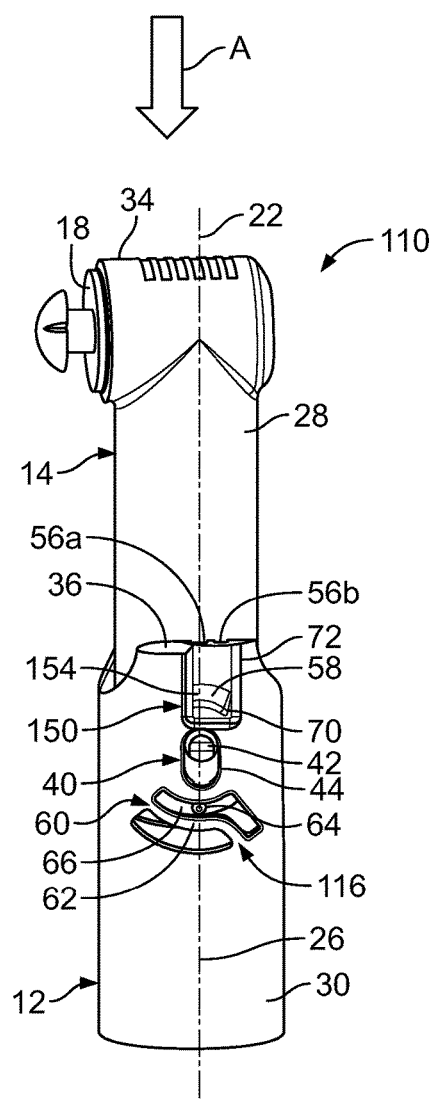
FIG. 7 is a partial side view of the prophy angle of FIG. 5 in a straight angular position.
Figure 8:
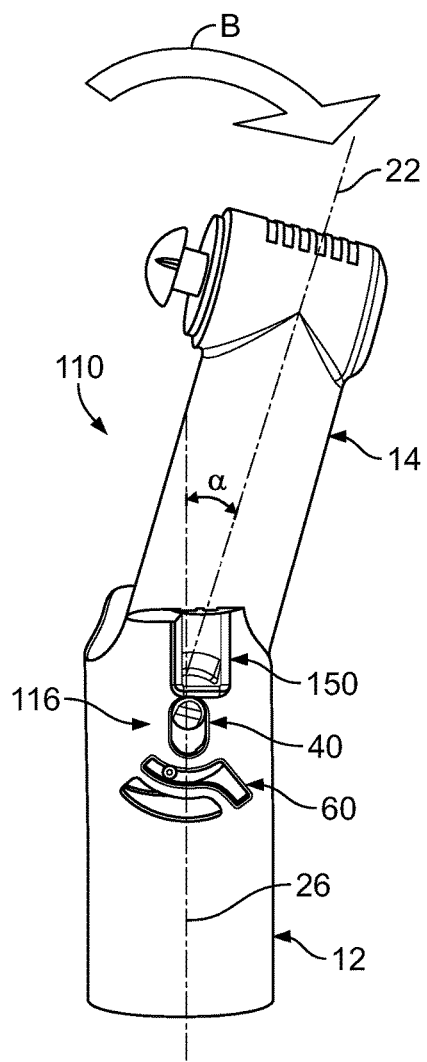
FIG. 8 is a partial side view of the prophy angle of FIG. 5 in a bent angular position.
Figure 11:
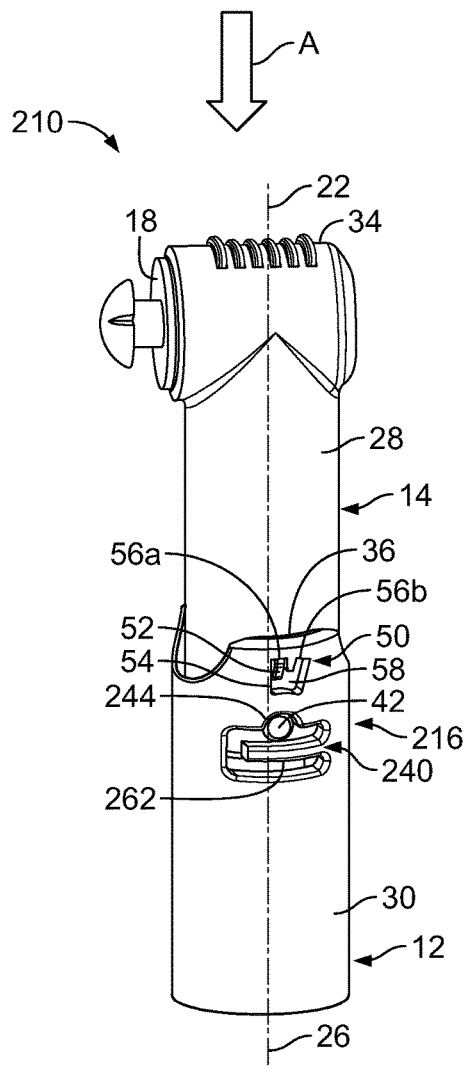
FIG. 11 is a partial side view of the prophy angle of FIG. 9 in a straight angular position.
Figure 12:
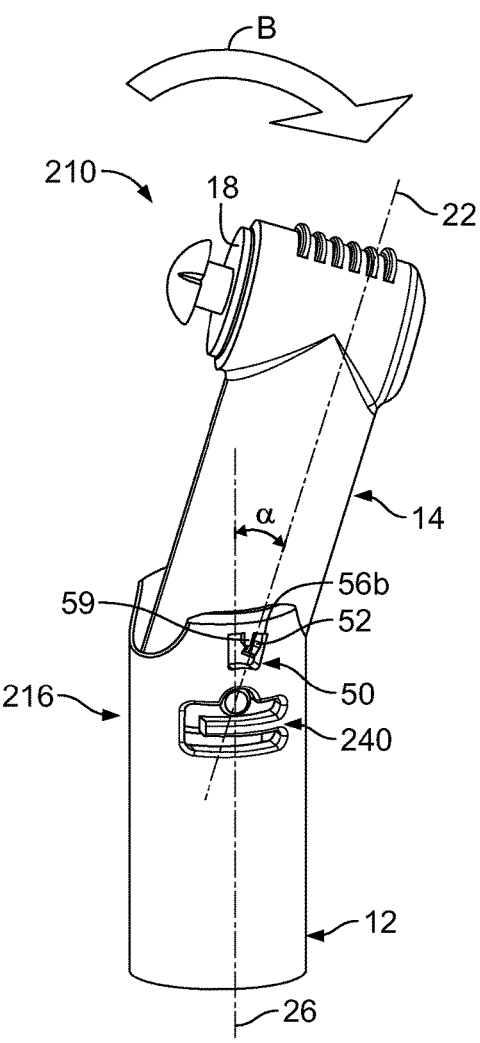
FIG. 12 is a partial side view of the prophy angle of FIG. 9 in a bent angular position.

Turning now more particularly to the adjustment mechanism 116, as best seen in FIG. 6, the adjustment mechanism 116 includes the pivot assembly 40. The pivot assembly 40 includes the pivot member 42 and the pivot receptacle 44, which are arranged to allow the tool head 14 to pivot and to slide relative to the hand piece 12, in the same manner as previously described.

The adjustment mechanism 116 may include an angular lock assembly 150. The angular lock assembly 150 allows the tool head 14 to be selectively locked in any one of a plurality of angular positions relative to the hand piece 12. The angular lock assembly 150 allows the tool head 14 to be axially shifted relative to the hand piece 12 between a locked position and an adjustment position. The angular lock assembly allows the tool head 14 to be angularly adjusted between a plurality of selected angular positions relative to the hand piece 12 in the adjustment position. The angular lock assembly 150 locks the tool head 14 in a selected one of the angular positions when the tool head is in the locked position. In the present example, the angular lock assembly 150 is arranged to allow the tool head 14 to be selectively locked in either of the first angular position or the second angular position. However, different and/or additional angular positions are also possible. In the present example, the angular lock assembly 150 includes the tab 52 and a receiver 154. The tab 52 is substantially similar to the tab 52 as previously described. The receiver 154 is similar to the receiver 54 in that it includes first and second locking slots 56a and 56b arranged in a V-shaped configuration with the proximal ends of the locking slots connected by a transverse track 58; however, the locking slots 56a and 56b do not extend all the way through the wall of the housing 30, but rather are formed by grooves disposed on an interior surface of the housing 30. The transverse track 58 is preferably aligned with a window 70 through the wall of the housing 30, such that the tab 52 is visible through the window when the tool head 14 is in the adjusting position, thereby providing a visual confirmation that the tool head 14 is in the adjustment position. In addition, a recess 72 on the exterior surface of the housing 30 is optionally aligned with the window 70. The recess 72 is preferably sized to receive the pad of a finger of the user so that the user can feel when the tab 52 is in the window 70, thereby providing a tactile confirmation that the tool head 14 is in the adjustment position. The angular lock assembly 150 functions substantially the same as the angular lock assembly 50. The reader is invited to refer to the detailed explanations thereof provided previously.

The adjustment mechanism 116 preferably includes the spring assembly 60 as previously described herein, including a spring 62, a spring follower 64, and a lateral track 66. The reader is invited to refer to the detailed explanations of the spring assembly 60 provided previously herein.

The process of adjusting the prophy angle 110 is substantially similar as the process described with reference to FIGS. 3 and 4, and the reader is invited to refer to those portions of the description for further detail if desired.

FIGS. 9-12 exemplify another prophy angle 210 according to the teachings of the present application. The prophy angle 210 is similar to the prophy angles 110 and 10 except for differences in the adjustment mechanism 216 as explained in detail hereinafter. Thus the prophy angle 210 also includes a tool head 14 that is pivotably and slidably coupled to a hand piece 12, wherein the tool head 14 can be selectively adjusted between a plurality of angular positions including a first angular position, such as a straight position (see FIG. 11), and a second angular position, such as a bent position (see FIG. 12). The prophy angle 210 also includes a flexible drive linkage 24 that operatively connects a drive unit carried in the hand piece 12 with a tool drive 18 carried by the tool head 14. These and other remaining features of the prophy angle 210 that are not otherwise described hereinafter are substantially similar to the same features as described previously with respect to the prophy angle 10, and the reader is invited to refer to such description for additional details related thereto.

Turning now more particularly to the adjustment mechanism 216, as best seen in FIG. 10, the adjustment mechanism includes a pivot assembly 240 that allows the tool head 14 to be both pivoted and axially shifted with respect to the hand piece 12. The adjustment mechanism 216 also preferably includes the angular lock assembly 50 described previously herein; however, the adjustment mechanism 216 could also be implemented with the angular lock assembly 150 also described previously herein. Thus, the reader is invited to refer to the descriptions of the lock assemblies 50 and 150 for additional details thereof.

Unlike the previous exemplary pivot assemblies, the pivot assembly 240 combines the functionality of a spring assembly and a pivot assembly into a combined set of features rather than as to separate features. Thus, in this arrangement, the pivot assembly 240 includes a pivot member 42 which is pivotably received within a pivot receptacle 244, and a spring 262 resiliently retains the pivot member 42 in the pivot receptacle 244 in a manner that allows the pivot member 42 two both rotate about is axes and to shift axially relative to the housing 30 between the locked position in the adjustment position. The spring 262 is in the form of a cantilevered resilient arm defined in a cut away portion of the wall of the housing 30. The pivot receptacle 244 is in the form of an arcuate receptacle, such as a semi-circular cutout from the wall of the housing 30, disposed along a distal end of the cut away portion of the wall of the housing. The pivot member 42 is pivotably received within the pivot receptacle 244, but is not completely surrounded by the pivot receptacle 244. Rather, the spring 262 is in the form of a cantilevered spring arm formed by a section of the wall of the housing 30 that extends laterally across the cut away portion of the wall and resiliently urges the pivot member 42 upwardly, i.e., in the direction toward the distal and 36 of the housing 30. Thus, the spring 262 resiliently retains the pivot member 42 in the pivot receptacle 244. However, the spring 262 allows the pivot member 42 to be resiliently urged in the direction of the proximal end of the hand piece 12, such as by sliding downwardly in the pivot receptacle 244, a distance less than the height of the pivot member 42 that is fully received within the pivot receptacle 244. Thus, the spring 262 allows the tool head 14 to slide axially relative to the hand piece 12 between the locked position and the adjustment position previously described. The spring 262 also prevents the pivot member 42 from being moved axially all the way out of the pivot receptacle 244, thereby retaining the pivot member 42 within the pivot receptacle 244 in both the adjustment position and the locked positions. However, the spring 262 could take other forms suitable for functioning in the same or generally similar manner.

A process of adjusting the prophy angle 210 is generally similar to the process of adjusting the prophy angles 10 and 110, except that instead of the pivot member 42 sliding axially along a slot 44, in this arrangement, the pivot member 42 simply slides axially within the pivot receptacle 244 against the resilient movement of the spring 262. Otherwise, adjustment of the prophy angle 210 between the first angular position and the second angular position is carried out in substantially the same manner as previously described and the reader is invited to refer to the previous detailed description provided thereof.

Turning now to FIGS. 13 and 14, a further prophy angle 310 according to the teachings of the present application is shown, which is generally similar to the prophy angle 110, but with an adjustment mechanism 316 having a different spring assembly 350. Thus the prophy angle 310 also includes a tool head 14 that is pivotably and slidably coupled to a hand piece 12, wherein the tool head 14 can be selectively adjusted between a plurality of angular positions including a first angular position, such as a straight position (see FIG. 13), and a second angular position, such as a bent position (see FIG. 14) as previously described. The prophy angle 310 also includes a flexible drive linkage 24 that operatively connects a drive unit carried in the hand piece 12 with a tool drive 18 carried by the tool head 14 as previously described. The prophy angle 310 also includes a pivot assembly 40 and an angular lock assembly 150 as previously described; however, the angular lock assembly 50 could also be used. These and other remaining features of the prophy angle 310 that are not otherwise described hereinafter are substantially similar to the same features as described previously and the reader is invited to refer to such description for additional details related thereto.

Turning now more particularly to the spring assembly 350 (best seen in FIG. 14), the spring assembly 350 in this arrangement includes a spring 362 that is carried on a spring seat 380 disposed within the housing 30 of the hand piece 12 and arranged to press against the proximal end 32 of the housing 28 of the tool head 14. In the exemplary arrangement, the spring 362 is in the form of a saucer-shaped disc or washer. The saucer-shaped form provides the spring 362 with a resilient flexible quality. The spring seat 380 is in the form of an inner annular seating surface, such as an inner annular flange or a series of inner annular projections, along an in interior surface of the housing 30. The apex of the spring 362 presses against the proximal end 32 of the housing 28, and the outer annular periphery of the spring 362 is supported by the spring seat 380. The spring 362 presses the tool head 14 axially away from the hand piece 12 and into the locked position. Pressing the tool head 14 axially toward the hand piece 12 resiliently flexes the spring 362 downwardly into a flatter shape, thereby allowing the tool head 14 to be shifted into the adjustment position previously described. When in the adjustment position, the tool head 14 can be angularly adjusted between the various angular positions. When the tool head 14 is arranged in a selected one of the angular positions, the pressure on the tool head 14 can be released, and the spring 362 automatically presses the tool head 14 axially back into the locked position at the selected one of the angular positions. The remaining portions of the prophy angle 310 function substantially as previously described herein, and the reader is invited to refer to the previous detailed descriptions thereof.

The exemplary arrangements shown in the drawings and described in detail herein are not intended to be limiting, but rather are provided as just a few examples out of many possible arrangements to enable the person of ordinary skill to make and use the invention. Additional arrangements, combinations of features, and/or advantages of the invention are contemplated within the scope of the claims appended hereto.

What is claimed:

1. A dental prophylaxis angle, comprising:
 a tool head having a first longitudinal axis and a tool drive;
 a hand piece having a second longitudinal axis and being pivotably connected to the tool head;
 an adjustment mechanism configured to allow the tool head to be angularly adjusted laterally relative to the second longitudinal axis between a plurality of angular positions relative to the hand piece, wherein the adjustment mechanism comprises a pivot assembly that pivotably and slidably connects the tool head to the hand piece, wherein the pivot assembly includes a pin projecting laterally relative to the first and second longitudinal axes, wherein the pin is carried by an exterior surface of one of the tool head and the hand piece, the pin pivotably received within a pivot receptacle defined in the other of the tool head and the hand piece, the pivot receptacle being located in a housing extending longitudinally between a proximal end and a distal end of the other of the tool head and the hand piece, and
 a drive linkage connected to the tool drive, wherein the drive linkage extends longitudinally along each of the tool head and the hand piece,
 wherein the pin of the adjustment mechanism slides longitudinally along the pivot receptacle and thereby allows the tool head to be axially shifted relative to the hand piece along at least one of the first longitudinal axis and the second longitudinal axis between a locked position and an adjustment position,
 wherein the adjustment mechanism prevents the tool head from angularly pivoting laterally about the pin relative to the second longitudinal axis of the hand piece in the locked position, and
 wherein the adjustment mechanism enables the first longitudinal axis of the tool head to pivot laterally about the pin relative to second longitudinal axis of the hand piece and thereby be angularly adjusted in the adjustment position.

2. The dental prophylaxis angle of claim 1, wherein the pin is slidably received within the pivot receptacle and slides axially along at least one of the first and second longitudinal axes.

3. The dental prophylaxis angle of claim 2, wherein the pivot receptacle comprises an elongate recess extending longitudinally along one of the tool head and the hand piece.

4. The dental prophylaxis angle of claim 2, wherein the pivot receptacle comprises an open-sided socket having a wall portion defining a groove extending longitudinally along one of the tool head and the hand piece to pivotably and slidably receive the pivot member and an open portion opposite the recess.

5. The dental prophylaxis angle of claim 1, wherein the adjustment mechanism comprises:
 a spring assembly arranged to urge the tool head longitudinally into the locked position at the angular positions.

6. The dental prophylaxis angle of claim 5, wherein the spring assembly comprises a resilient member formed by a portion of a wall of the hand piece.

7. The dental prophylaxis angle of claim 6, wherein the spring assembly comprises a spring follower that is carried by the tool head and that engages the resilient member.

8. The dental prophylaxis angle of claim 6, wherein the resilient member directly engages the pin of the adjustment mechanism about which the tool head pivots laterally.

9. The dental prophylaxis angle of claim 5, wherein the spring assembly comprises a spring that is carried on a spring seat disposed within the hand piece, wherein the spring presses against the proximal end of the tool head.

10. The dental prophylaxis angle of claim 1, wherein the adjustment mechanism comprises:

an angular lock assembly arranged to releasably lock the tool head at any one of a plurality angular positions relative to the hand piece, wherein the angular lock assembly allows the tool head to be axially shifted longitudinally relative to the hand piece between the locked position and the adjustment position, wherein the angular lock assembly allows the tool head to be angularly adjusted laterally between the plurality of angular positions relative to the hand piece in the adjustment position, and wherein the angular lock assembly locks the tool head in a selected one of the angular positions when the tool head is in the locked position.

11. The dental prophylaxis angle of claim 10, wherein the lock assembly comprises:

a tab; and a receiver arranged to lockingly receive the tab at each of the plurality of predefined angular positions.

12. The dental prophylaxis angle of claim 11, wherein the receiver comprises a first locking slot and a second locking slot defined in one of the hand piece and the tool piece, each locking slot corresponding to a different one of the predefined angular positions.

13. A method of angularly adjusting a dental prophylaxis angle according to claim 1, the method comprising the steps:

urging the tool head axially along at least one of the first and second longitudinal axes relative to the hand piece into the adjustment position; and pivoting the tool head laterally relative to the hand piece about the pin from a first angular position to a second angular position while in the adjustment position.

14. The dental prophylaxis angle of claim 12, wherein the first locking slot and the second locking slot are arranged in a generally V-shaped form, with the first locking slot aligned axially with a first angular position and the second locking slot aligned axially with a second angular position.

15. The dental prophylaxis angle of claim 12, wherein the tab is received within one of the first locking slot and the second locking slot in the locked position so as to prevent pivoting of the tool head relative to the hand piece.

16. The method of claim 13, further comprising allowing a spring to urge the tool head axially into the locked position in the second angular position.

* * * * *